United States Patent [19] | [11] Patent Number: 5,061,381
Burd | [45] Date of Patent: Oct. 29, 1991

[54] APPARATUS AND METHOD FOR SEPARATING CELLS FROM BIOLOGICAL FLUIDS

[75] Inventor: Tammy L. Burd, Santa Clara, Calif.

[73] Assignee: Abaxis, Inc., Mountain View, Calif.

[21] Appl. No.: 532,524

[22] Filed: Jun. 4, 1990

[51] Int. Cl.5 .................. B01D 21/26; B04B 5/02; B04B 11/00

[52] U.S. Cl. ........................... 210/789; 210/94; 210/198.1; 210/380.1; 210/514; 210/515; 210/532.1; 422/64; 422/72; 422/102; 422/101; 436/45; 436/63; 436/177; 436/180; 494/16; 494/17; 494/29; 494/37; 494/43

[58] Field of Search ............. 210/94, 95, 380.1, 514, 210/515, 518, 782, 787, 789, 198.1, 512.1, 532.1; 422/64, 72, 101, 102; 494/16, 27, 29, 37, 43, 17; 436/45, 63, 177, 180

[56] References Cited

U.S. PATENT DOCUMENTS

| 2,885,145 | 5/1959 | Danielsson et al. | 494/10 |
| 3,241,752 | 3/1966 | Ende | 494/16 |
| 3,707,354 | 12/1972 | Goodman | 422/72 |
| 3,901,658 | 8/1975 | Burtis et al. | 422/72 |
| 4,632,908 | 12/1986 | Schultz | 436/156 |
| 4,740,472 | 4/1988 | Burtis et al. | 210/787 |
| 4,776,832 | 10/1988 | Martin et al. | 494/19 |
| 4,788,154 | 11/1988 | Guigan | 436/180 |
| 4,798,579 | 1/1989 | Penhasi | 494/16 |
| 4,814,282 | 3/1989 | Holen et al. | 436/165 |
| 4,835,106 | 5/1989 | Johnson et al. | 436/45 |
| 4,847,205 | 7/1989 | Burtis et al. | 436/45 |

FOREIGN PATENT DOCUMENTS

| 0160282 | 11/1985 | European Pat. Off. . |
| 0195321 | 9/1986 | European Pat. Off. . |
| 226518 | 6/1987 | European Pat. Off. . |
| 251946 | 1/1988 | European Pat. Off. . |
| 262060 | 3/1988 | European Pat. Off. . |
| 2589240 | 4/1987 | France . |

OTHER PUBLICATIONS

Analyse Biologique, Clinical Biology, Satelit 900, 6 pages.
Truchaud et al. (1987), Clinical Chemistry 33:1560.

Primary Examiner—W. Gary Jones
Attorney, Agent, or Firm—Townsend and Townsend

[57] ABSTRACT

A centrifugal rotor for separating plasma from whole blood includes a plurality of internal chambers and passages for combining the plasma with one or more reagents and distributing the plasma to a plurality of individual test wells. The chambers and passages necessary for separating the whole blood into plasma are located on a first, upper level within the rotor and include a measuring chamber, an overflow chamber, a separation chamber, and a reagent chamber. The measuring chamber and overflow chamber have capillary dimensions so that an initial volume of whole blood partitions therebetween, with the measuring chamber filling first to provide a preselected volume. The separation chamber is located radially outward from both the measuring chamber and the reagent chamber to that spinning of the rotor causes both the reagent and the measured blood volume to flow outward into the separation chamber. The separation chamber includes a radially-outward cell trap and a radially-inward drainage port so that spinning of the rotor causes the cellular components of the whole blood to enter the cell trap, while cessation of spinning allows the separated plasma to flow downward through the drainage port. A collection chamber is formed at a lower level than the rotor to receive the plasma through the drainage port. Further spinning of the rotor causes the plasma to flow radially outward into a plurality of test wells formed around the periphery of the collection chamber. Testing of the separated plasma volumes may be performed without removing the plasma from the rotor.

29 Claims, 6 Drawing Sheets

APPARATUS AND METHOD FOR SEPARATING CELLS FROM BIOLOGICAL FLUIDS

BACKGROUND OF THE INVENTION

1. Field of the Invention

The present invention relates generally to apparatus and methods for separating cellular material from biological fluids and, more particularly, to the design and use of a centrifugal rotor which is capable of separating plasma from an applied volume of whole blood and optionally distributing the plasma to a plurality of test wells within the rotor.

Blood tests frequently require that potentially-interfering cellular components of the blood be separated from the blood plasma prior to testing of the plasma. It is also frequently desirable to divide the separated blood plasma into a plurality of discrete aliquots so that a variety of tests or assays may be performed on the blood. Such separation and division steps have heretofore been typically performed by centrifugation to separate the blood plasma from the cellular components, followed by manual or automated pipetting of the blood plasma into separate test wells. Such procedures are labor intensive and time-consuming, and various automated systems and methods have been proposed for providing multiple aliquots of plasma suitable for testing in a more efficient manner.

Of particular interest to the present invention are centrifugal rotors which have been modified both to separate plasma from whole blood and to distribute the separated plasma into separate test wells. The use of such rotors can provide a plurality of discrete plasma volumes which may be tested or evaluated, all present within the centrifugal rotor, greatly enhancing the efficiency of automated testing procedures.

Although a significant improvement over prior manual or partly manual procedures, previous modified centrifugal rotors have suffered from a number of deficiencies. Such rotors have frequently required the application of relatively large volumes of whole blood in order to achieve the desired separation and distribution. The efficiency of separation has frequently been low, typically on the order of 5% based on the initial amount of plasma available. Moreover, such rotors have frequently utilized complex designs which are difficult and costly to manufacture. Often, the rotors require various separable parts or components which are brought together or separated at different points in the centrifugation procedure. Previous centrifugal rotors have often been limited in the number of discrete samples and test wells which they can provide, and in some cases require the use of a separate displacement fluid to effect flow of blood and plasma through the system.

For these reasons, it would be desirable to provide improved centrifugal rotors and methods suitable for separating blood into plasma and cellular components and for further distributing the separated plasma into a plurality of discrete test wells within the rotors. The rotors should be capable of separating relatively small volumes of blood and should not require the use of a displacement fluid for effecting such separation. In particular, it would be desirable to have a separation efficiency greater than 10%, preferably greater than 20%, and more preferably greater than 30%. The rotors should be able to accommodate relatively large numbers of test wells, and the rotor design should be simple and amenable to low-cost manufacturing procedures. In particular, it would be desirable if the rotors were of unitary construction with no separable or movable parts. Plasma separation methods should be simple and be capable of being performed in relatively short times. In particular, the methods should require relatively few steps and should be capable of being performed with little or no intervention or manipulations by the operator. It would be particularly desirable if the methods required only rotation of the rotor in order to effect both the separation and distribution of the plasma.

2. Description of the Background Art

U.S. Pat. No. 3,901,658, describes a centrifugal rotor which separates plasma from whole blood and transfers the plasma to a sample cuvette. The rotor requires use of a displacement liquid to force the plasma into the sample cuvette. U.S. Pat. No. 4,835,106, describes a centrifugal rotor which includes a plurality of removable capillary tubes for separating plasma from whole blood. The blood is introduced by placing a blood-filled capillary into a passage within the disk. U.S. Pat. Nos. 4,847,205 and 4,470,472, both describe centrifugal rotors which separate plasma from whole blood but which do not provide for in situ analysis. European patent application 160 282, discloses a test card which is used in a specialized centrifuge where a plurality of test cards are arranged annularly and where the cards may be rotated 90° relative to the rotor to apply orthogonal forces to the card. The card must be turned (relative to the rotor) numerous times during a test cycle to effect a desired separation and plasma flow. The specialized centrifuge is described in U.S. Pat. Nos. 4,814,282; 4,776,832; 4,632,908, and European patent application 195 321. A system for two-dimensional centrifugation commercially available from KIS Photo Industrie, Gieres, France, is identified by the SATELIT tradename. The system uses a disposable test pack with a separable capillary collector for whole blood, as described in more detail in Truchaud et al. (1987), *Clin. Chem.* 33:1560. See also European patent application nos. 226 518; 251 946; 262 060, and French patent application 2 589 240. Other centrifugal rotor designs are described in U.S. Pat. Nos. 4,798,579; 3,707,354; 3,241,752; and 2,885,145.

SUMMARY OF THE INVENTION

According to the present invention, an improved cell separator comprises a centrifugal rotor having top and bottom surfaces and a central axis therethrough. A separation chamber is disposed at a first level within the rotor whereby a biological fluid, e.g., whole blood can be separated into cell-free fluid, e.g., plasma and cellular components in response to spinning of the rotor. The separation chamber usually includes a receptacle region, a cell trap spaced radially outward from the receptacle region, and a capillary region between the receptacle region and the cell trap. In the exemplary embodiment, the capillary region is an annular space having inner and outer arcuate boundaries formed between opposed surfaces (separated by a capillary distance). The cell trap is formed contiguously with the outer arcuate boundary of the annular space, typically as an annular well. The receptacle region is formed contiguously with the inner arcuate boundary of the annular space, typically as a tapered compartment having a narrow aperture adjacent the annular space. In this way, spining of the rotor causes cells in the biological fluid to pass from the receptacle region through the capillary region into the cell trap. After spinning is stopped, the capillary region inhibits backflow of the cellular material from the cell trap into the receptacle region where the clear biological fluid, e.g., plasma, remains.

In a preferred embodiment, the rotor further includes the capability of distributing discrete aliquots of the separated fluid into test wells. A collection chamber is disposed beneath the separation means in the rotor, and an axial drainage port in the separation means allows plasma but not cellular components to flow downward into the collection chamber when spinning of the rotor is ceased, typically by gravity alone, by momentum change, or by capillary force. Conveniently, the collection chamber includes a plurality of test wells formed about its periphery so that further spinning of the rotor causes plasma in the collection chamber to flow radially outward into said test wells. Thus, separation of whole blood into plasma and distribution of the separated plasma into discrete test wells can be accomplished in as few as four steps, including application of whole blood to the rotor, spinning of the rotor to effect separation of the blood plasma, slowing or stopping the spinning of the rotor to allow the separated plasma to flow downward into the collection chamber, and finally spinning the rotor again to distribute the plasma into separate test wells. Of course, under certain circumstances, it may be desirable to provide additional steps in order to accomplish specific objectives. Such additional steps will, however, not generally be required in order to accomplish the essential separation and distribution steps of the present invention.

In the exemplary embodiment, at least one metering chamber is disposed in the rotor at the same level as the separation chamber and arranged so that the separation chamber lies radially outward from the metering chamber. The metering and separation chambers are interconnected so that whole blood applied to the metering chamber will flow into the separation chamber as the rotor is spun. Usually, a separate reagent chamber will be provided on the same level as the separation and metering chambers within the rotor. The reagent chamber will also be interconnected with the separation chamber and arranged so that spinning the rotor will cause flow of a liquid reagent or diluent from the reagent chamber into the separation chamber. In this way, reagents, diluents, or the like can be combined with the blood plasma during the initial separation step of the method.

DESCRIPTION OF THE SPECIFIC EMBODIMENTS

The present invention provides apparatus and methods for separating cellular components from biological fluids, and in particular for separating whole blood into plasma which may then be subjected to a wide variety of analytic procedures. Conveniently, the apparatus and methods will also provide for distribution of the separated plasma into a plurality of test wells within the rotor so that different analytic procedures may be performed without having to transfer aliquots of the plasma from the apparatus. The apparatus and method are able to separate very low volumes of blood, usually as low as about 0.03 cc, frequently as low as about 0.015 cc, and sometimes as low as about 0.005 cc, although the present invention is suitable for separating much larger volumes as well. The present invention does not require the use of a displacement medium for effecting the desired separation and distribution, and the apparatus design is very simple with no separate or moving parts required. Of course, it may be desirable in certain circumstances to provide such separate or moving parts, but they are not required in order to achieve the blood separation according to the method of the present invention. As a result, the apparatus is very easy to manufacture and can be produced at a very low cost, making the apparatus suitable for use as a disposable in testing whole-blood samples. The apparatus and method are able to separate precise volumes of blood without the need to premeasure the amount applied to the apparatus. The apparatus can further provide for automatic combination of the separated plasma with a reagent or diluent and can apportion substantially equal volumes of plasma among the plurality of test wells. In addition, the apparatus is suitable for use with a variety of conventional analytic measurement devices, such as spectrophotometers and fluorometers, which allow the plasma in the test wells to be individually examined without the need to remove the plasma from the wells.

Although the present invention is particularly suitable for separating cells from blood to produce plasma, it will be useful with a wide variety of other biological fluids, such as urine, sputum, semen, saliva, ocular lens fluid, cerebral fluid, spinal fluid, amniotic fluid, and tissue culture media, as well as food and industrial chemicals, and the like, where it may be desirable to separate cells and other interfering substances prior to analysis or assay.

The apparatus of the present invention includes a centrifugal rotor which is capable of being mounted on a conventional laboratory centrifuge of the type which is commercially available from suppliers, such as Beckman Instruments, Inc., Spinco Division, Fullerton, Calif.; Fisher Scientific, Pittsburgh, Pa.; VWR Scientific, San Francisco, Calif., and the like. Generally, the centrifugal rotors will include a receptacle or other coupling device suitable for mounting on a vertical drive shaft within the centrifuge. The particular design of the receptacle or coupling device will depend on the nature of the centrifuge, and it will be appreciated that the centrifugal rotor of the present invention may be adapted to be used with most types of centrifuges which are now available or which may become available in the future.

The centrifugal rotor comprises a body structure which maintains a desired geometric pattern or relationship between a plurality of chambers and interconnecting passages, as described in more detail hereinbelow. Usually, the body will be a substantially solid plate with the chambers and passages formed as spaces or voids in an otherwise solid matrix. Conveniently, such solid plate structures may be formed by laminating a plurality of separately formed layers together into a composite structure where the chambers and passages are generally formed between adjacent layers. The individual layers may be formed by injection molding, machining, and combinations thereof, and will usually be joined together, typically using a suitable adhesive or by ultrasonic welding. The final enclosed volumes are formed when the layers are brought together. Of course, the centrifugal rotor could also be formed as a plurality of discrete components, such as tubes, vessels, chambers, etc., arranged in a suitable structural framework. Such assemblies, however, are generally more difficult to manufacture and are therefore less desirable than those formed in a substantially solid plate.

The centrifugal rotor may be formed from a wide variety of materials and may optionally include two or more materials. Usually, the materials will be transparent so that the presence and distribution of blood, plasma, and other reagents, may be observed within the various internal chambers and passages. Also, it is generally required that the test wells formed within the rotor have suitable optical paths formed therethrough so that the contents of the test well may be observed spectrophotometrically, fluorometrically, or by other visual assessment instruments. In the exemplary embodiment described below, the rotor is formed from acrylic resins having the required optical properties, at least in those areas which define the optical paths.

The apparatus and method of the present invention are suitable for performing a wide variety of analytic procedures which are beneficially or necessarily performed on blood plasma. The analytic procedures will generally require that the blood plasma be combined with one or more reagents so that some visibly detectable change occurs in the plasma which may be related to measurement of a particular component or characteristic of the plasma. Preferably, the plasma will undergo a reaction or other change which results in a change in color, fluorescence, luminescence, or the like, which may be measured by conventional spectrophotometers, fluorometers, light detectors, etc. In some cases, immunoassays and other specific binding assays may be performed in the test wells. Generally, however, such assay procedures must be homogeneous and not require a separation step. In other cases, it will be possible to accommodate heterogeneous assay systems by providing a means to separate blood plasma from the test wells after an immunological reaction step has occurred.

Conventional blood assays which may be performed include glucose, lactate dehydrogenase, serum glutamic-oxalacetic transaminase (SGOT), serum glutamic-pyruvic transaminase (SGPT), blood urea (nitrogen) (BUN), total protein, alkalinity, phosphatase, bilirubin, calcium, chloride, sodium, potassium, magnesium, and the like. This list is not exhaustive and is intended merely as being exemplary of the assays which may be performed using the apparatus and method of the present invention. Usually, these tests will require that the blood plasma be combined with one or more reagents which result in a visually detectable, usually photometrically detectable, change in the plasma. The reagents which are required are well known and amply described in the patent and scientific literature.

Referring now to FIGS. 1-6, a centrifugal rotor 10 constructed in accordance with the principles of the present invention will be described in detail. The rotor 10 is in the form of a substantially solid disk including a top layer 12, middle layer 14, and bottom layer 16 laminated together to form a composite structure. Typically, each of the layers 12, 14, and 16 will be composed of the same material, usually a transparent plastic such as an acrylate, but it is possible that the layers will be composed of different materials and that each layer may include two or more different materials forming different portions of the layer. The exposed surface of top layer 12 will be referred to as the top surface while the exposed surface of the bottom layer 16 will be referred to as the bottom surface. A receptacle 18 is formed in the bottom surface of layer 16 and is generally aligned with the vertical axis 20 of the rotor, as best observed in FIGS. 3 and 4. The receptacle 18 is formed to mate with the drive shaft of a conventional centrifuge system, as described previously.

Figure 1:
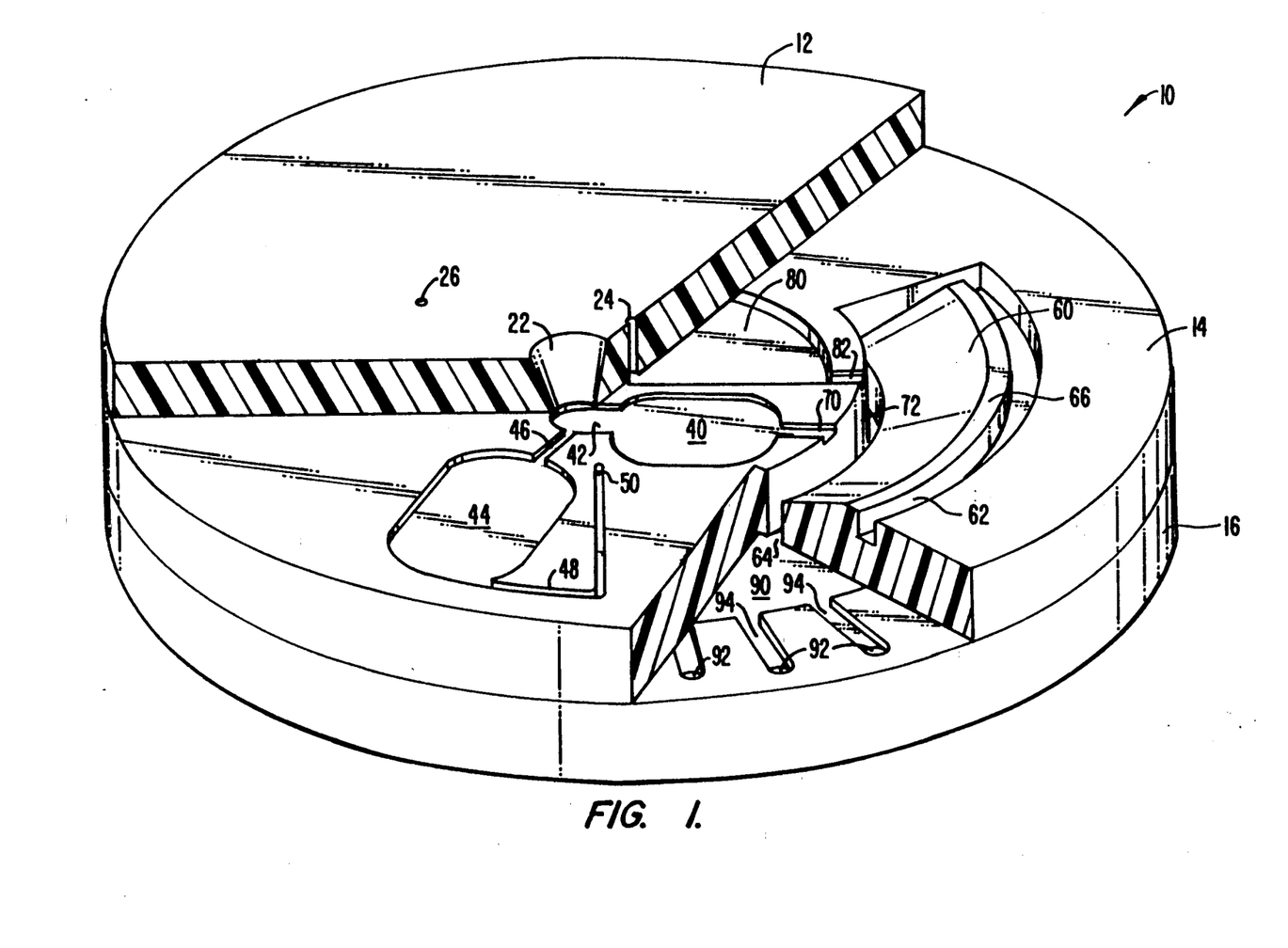
FIG. 1 is a perspective view of a centrifugal rotor constructed in accordance with the principles of the present invention, with portions broken away.
Figure 2:
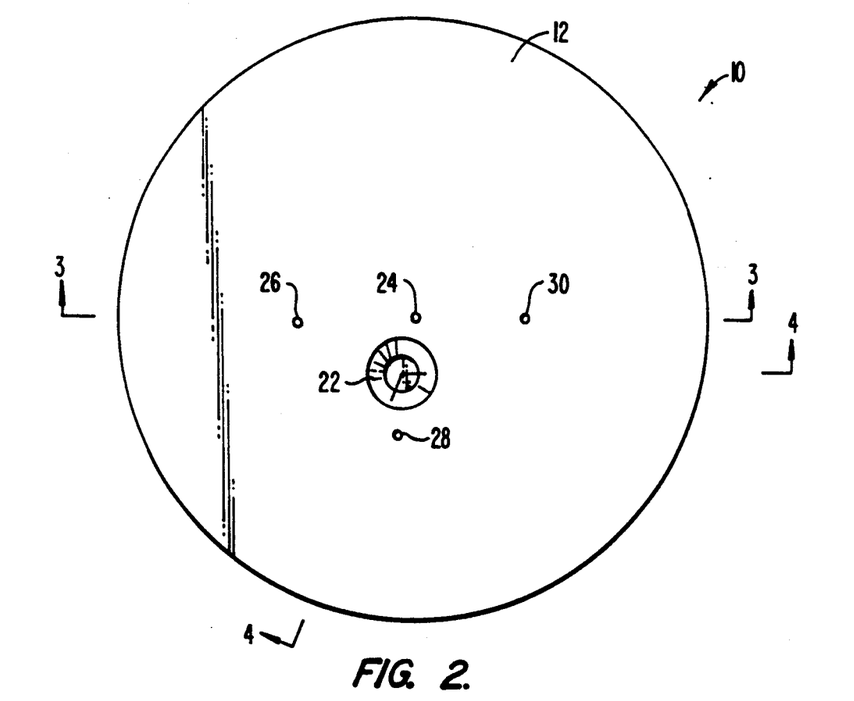
FIG. 2 is a top plan view of the centrifugal rotor of FIG. 1.

The top surface 12 includes a blood application port 22 and four vent ports 24, 26, 28, and 30. The blood application port 22 and vent ports 24, 26, 28, and 30, penetrate the entire thickness of the top layer 12 and, as described in more detail hereinbelow, are aligned with various chambers formed in the middle layer 14 of the rotor 10. These penetrations may conveniently be formed in the top layer 12 by machining, e.g., drilling.

The upper surface of middle layer 14 includes a plurality of chambers and passages formed therein. The chambers and passages may be formed by machining a disk having generally flat surfaces or may be formed by injection molding of a suitable plastic resin in order to initially form the disk.

The middle layer 14 includes a metering chamber 40 having an inlet segment 42 which is generally aligned with the blood application port 22 in top layer 12. The metering chamber 40 is connected to an overflow chamber 44 by a connecting passage 46, with the overflow chamber being located radially outward from the metering chamber. A vent connector passage 48 extends from the radially-outward end of overflow chamber 44, first in a generally annular direction and thereafter in a generally radially-inward direction. The distal terminus 50 of passage 46 is aligned with vent port 28 in top layer 12 so that the outward radial extremity of overflow chamber 44 will be vented to the atmosphere during use of the rotor 10.

The depth of metering chamber 40 and overflow chamber 44 will be selected to provide for capillary dimensions when the chambers are completed by lamination of the top layer 12. Typically, the depth will be in the range from about 0.1 to 1.0 mm, more typically being in the range from about 0.25 to 0.75 mm. Usually, the depth will be uniform for both chambers 40 and 46 as well as the connecting passage 46, although it will be possible to vary the depth so long as capillarity is maintained.

A separation chamber 60 is formed in the upper surface of middle layer 14 and is disposed radially outward from the metering chamber 40. The separation chamber 60 includes a cell trap 62 formed at its radially-outward periphery and a receptacle region 65 formed along its radially-inward perimeter. A capillary region 66 is formed between the receptacle region 65 and the cell trap 62 in order to inhibit the backflow of cells after they have entered the cell trap 62 as a result of centrifugal separation. The receptacle region 65 provides a volume which is capable of receiving whole blood or other biological fluid (optionally combined with a diluent or reagent) and which retains the blood plasma or other separated fluid after centrifugation has been completed. An axial port 64 is conveniently formed as an annular passage which penetrates the entire thickness of middle layer 14 so that separated plasma may flow downward from receptacle region 65 of chamber 60 into a collection chamber 90 formed in bottom layer 16, as described in more detail hereinafter. The geometry of the separation chamber 60 may be varied considerably, as discussed in more detail in connection with FIGS. 1A and 1B, below.

The metering chamber 40 is connected to the separation chamber 60 by a short capillary passage 70 which terminates in a vertical wall 72 which forms the inner surface of axial port 64. Such termination of passage 70 will, of course, terminate the capillarity which would otherwise draw fluid through the passage.

The volume of metering chamber 40 will vary depending on the desired application, but will usually be selected to be as low as possible to provide a desired amount of plasma to each of the test wells formed in bottom layer 16, as described in more detail hereinafter. Typically, the volume of metering chamber 40 will be in the range from about 0.005 to 0.05 cc, more typically being in the range from about 0.030 to 0.040 cc.

The volume of overflow chamber 44 will generally be larger than that of the metering chamber 40 in order to accommodate excess blood which may be applied through blood application port 42. Generally, the volume of the overflow chamber 44 will be at least twice that of the metering chamber 40, typically being three or more times larger.

The volume of separation chamber 60 will be selected to accommodate the expected volume of plasma and optionally reagent or dilent which can flow from the metering chamber 40 and reagent chamber 80 (as described below). Typically, the volume of the receptacle region 65 will be in the range from about 0.1 cc to 1.0 cc, more typically being in the range from about 0.25 cc to 0.50 cc. The volume of the cell trap 62 will depend at least in part on the volume of the receptacle region 65. In order to maximize the efficiency of separation, i.e., increase the amount of plasma obtained from a fixed amount of whole blood, it is desirable that the volume of the cell trap 62 be just large enough to accommodate the largest expected volume of cellular material. For whole blood this can be calculated based on the highest expected hematocrit, where the volume of cell trap 62 will then be the expected percentage of the volume of metering chamber 40. Usually, the volume of cell trap 62 will be from about 100% to 200% of the volume of metering chamber 40.

A reagent chamber 80 is also formed in the upper surface of middle layer 14 and connected to the separation chamber 60 through a capillary passage 82. The reagent chamber 80 will be disposed radially inward from the separation chamber 60 so that flow of reagent or diluent from the reagent chamber to the separation chamber 60 may be effected by spinning the rotor 14, as will be described in more detail hereinafter. As illustrated, the capillary passage 80 terminates with an open channel in wall 72. In this way, flow of reagent from chamber 80 will not occur in the absence of outward centrifugal force resulting from spinning of the rotor 10. In many cases, however, it may be desirable to provide a removable seal or barrier in chamber 82, or contain the reagent within a pouch or other package, to preserve the reagent and further assure that the reagent will not leak from chamber 80. Such a barrier, seal or package will be particularly desirable when the reagent is "prepackaged" into the centrifugal rotor 10 at a central preparation facility and later subjected to shipping, storing, and other handling procedures which might otherwise cause the reagent to degrade or leak.

Figure 3:
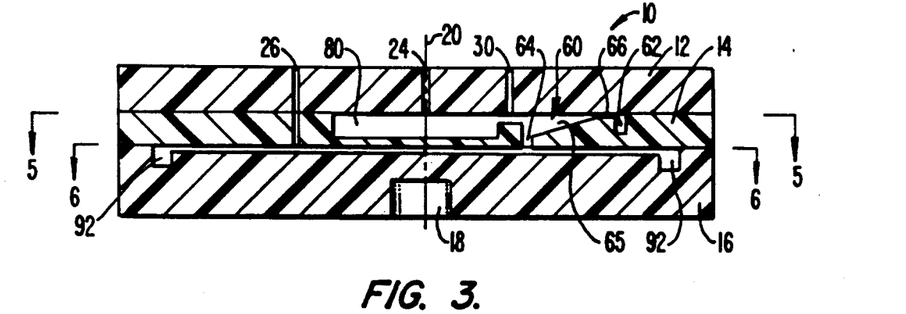
FIG. 3 is a vertical cross-sectional view of the rotor of FIGS. 1 and 2, taken along line 3—3 in FIG. 2.

As best observed in FIG. 3, the reagent chamber 80 may have substantially greater depth than the metering chamber 40 since the ability to provide capillary flow is not necessary. Thus, it is easy to store volumes of reagent which are substantially greater than the volume of blood or plasma which is provided to separation chamber 60 from metering chamber 40.

Figure 6:
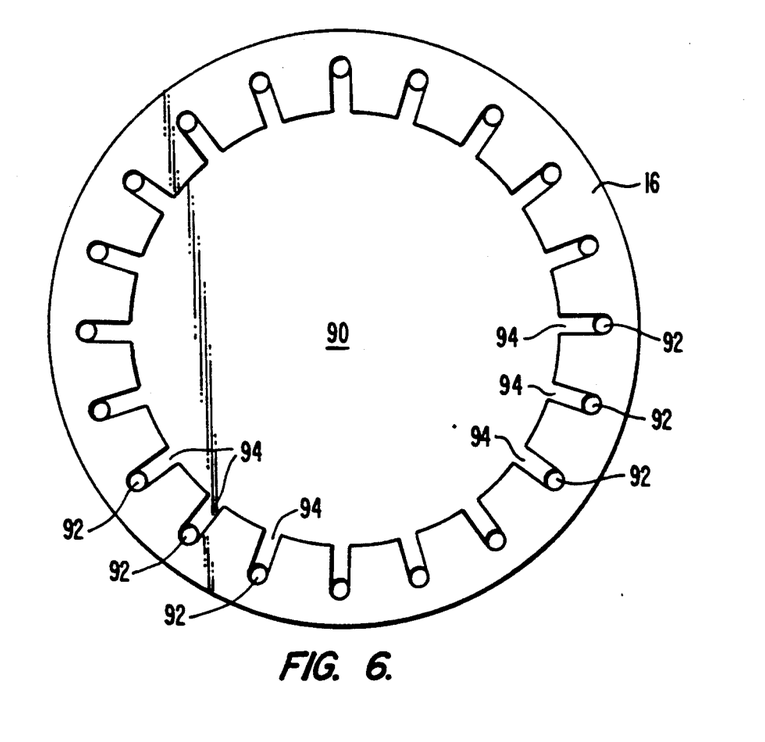
FIG. 6 is a horizontal cross-sectional view of the rotor of FIGS. 1-3, taken along line 6—6 in FIGS. 3 and 4.

A collection chamber 90 is formed in the upper surface of bottom layer 16 and is disposed to receive plasma from the axial port 64. A plurality of test wells 92 is formed about the periphery of the collection chamber 90 and connected by short radial passages 94. Generally, the test wells 92 will be spaced equally about the periphery of layer 16 in order to enhance the equal distribution of plasma to each of the test wells. The material above and below each test well 92 will usually be optically transparent in order to provide a clear optical path for visual assessment of the plasma in each well. Alternate optical paths through the rotor 10 may also be provided.

The volume of the test wells 92 will usually be relatively low, typically being in the range from about 0.005 cc to 0.015 cc, more usually being in the range from about 0.008 cc to 0.010 cc. It is possible that liquid, dried, or lyophilized reagents may be provided within the individual test wells so that combination occurs with the plasma when it is introduced. Alternatively, the walls or bottom of the test well 92 may be derivatized with various active components, such as antibodies, antigens, receptors, or the like, which are intended to take part in the analytic procedure.

Figure 1A:
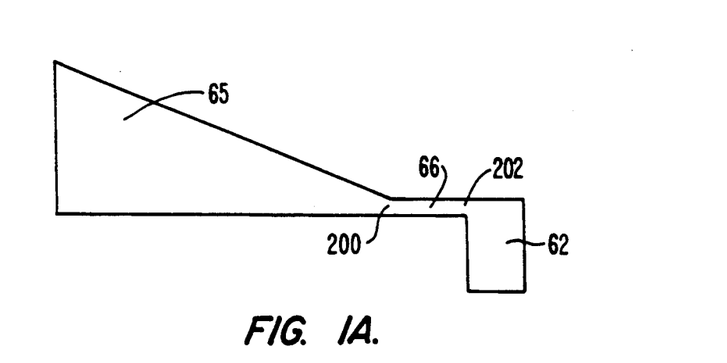
FIGS. 1A and 1B illustrate alternate geometries for a separation chamber of the type employed in a centrifugal rotor constructed in accordance with the principles of the present invention.
Figure 1B:
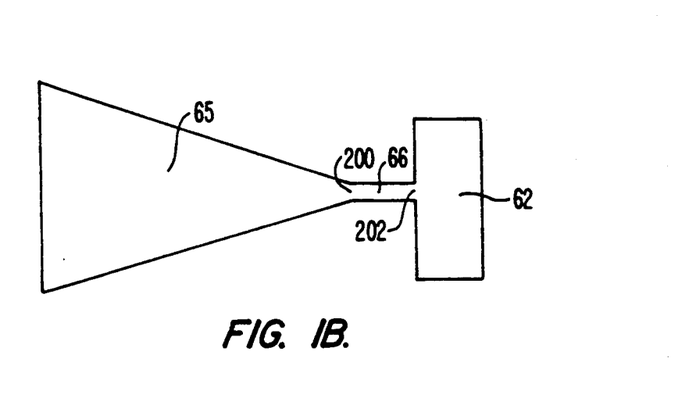

Referring now to FIGS. 1A and 1B, the geometry of the separation chamber 60 may be varied considerably within the scope of the present invention. The central feature of the separation chamber 60 is the capillary region 66, which is preferably an annular space having an inner arcuate boundary 200 and an outer arcuate boundary 202. The capillarity of region 66 is broken at each boundary 200 and 202 as the size of the adjoining regions, i.e., receptacle region 65 and cell trap 62, are increased to break the capillarity. Thus, fluid will be unable to flow through the capillary region 66 except when sufficient centrifugal force is applied by centrifugation.

The shapes of the receptacle region 65 and cell trap 62 may vary substantially. The receptacle region 65 will generally be tapered so that the distance between opposed horizontal surfaces increases in the radially inward direction. Such increasing distance provides the desired capillarity break, as discussed above. The taper may be provided by inclining the lower surface relative to the horizontal plane (FIG. 1), inclining the upper surface relative to the horizontal plane (FIG. 1A), or inclining both surfaces (FIG. 1B). The angle between the opposed surfaces of receptacle region 65 is not critical, typically being between 0° and 40°, and usually being between 18° and 22°. The inner arcuate boundary 200 of the capillary region is usually formed contiguously with the narrow end of the tapered receptacle region which defines an arcuate aperture.

The cell trap 62 is typically formed as an annular well which penetrates axially downward in the rotor and which is disposed contiguously with the outer arcuate boundary 202 of the annular space of the capillary region 66. The cell trap 62, however, may also extend upwardly, as illustrated in FIG. 1B, need not have a true annular shape.

Figure 4:
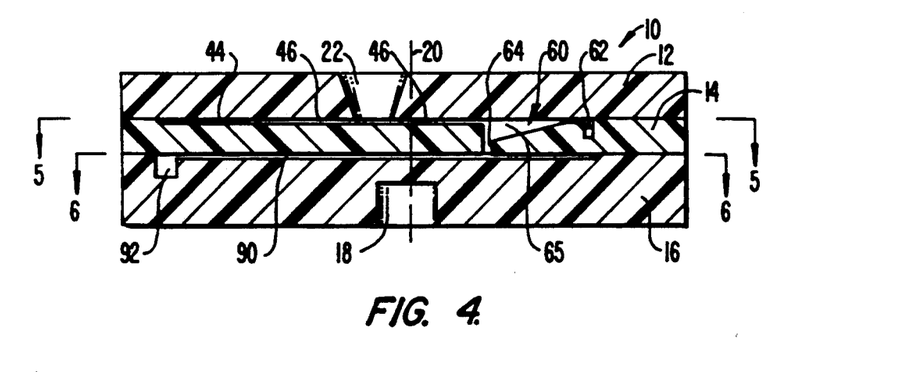
FIG. 4 is a vertical cross-sectional view of the rotor of FIGS. 1 and 2, taken along line 4—4 in FIG. 2.
Figure 4A:
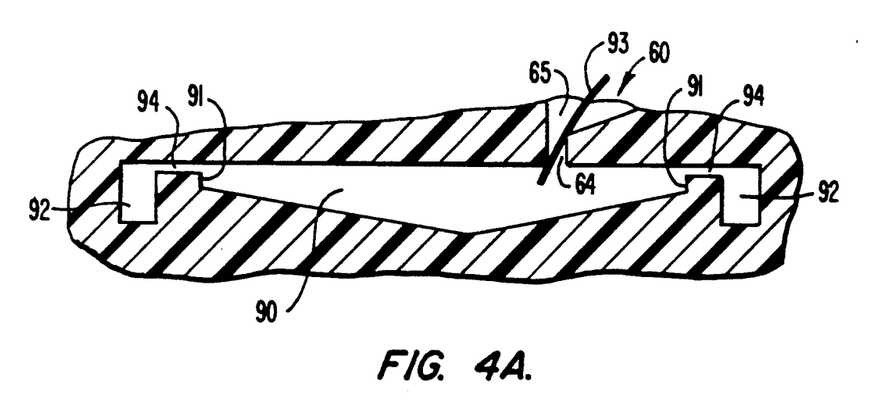
FIG. 4A is a cross-sectional view similar to that shown in FIG. 4, illustrating an alternative collection chamber geometry.
Figure 5:
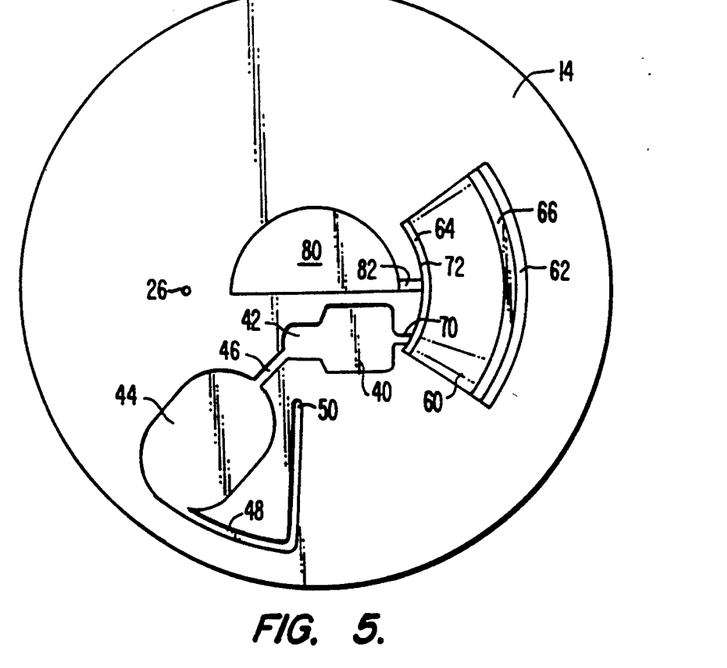
FIG. 5 is a horizontal cross-sectional view of the rotor of FIGS. 1-3, taken along line 5—5 in FIG. 3.

Referring now to FIG. 4A, the geometry of collection chamber 90 may be modified to promote mixing of the separated biological fluid, e.g., plasma, with a diluent or reagent combined in separation chamber 60. In particular, the volume of the collection chamber 90 may be increased and a peripheral vertical wall 91 may be provided inside of radial passages 94. Conveniently, the radial passage 94 will be capillaries which serve to prevent loss of fluid from the test wells 92 after the separation and distribution steps are completed. The increased volume of collection chamber 90 and peripheral wall 91 both act to increase the retention time of liquid in chamber 90 as the rotor 10 is spun. Such increased retention time allows more thorough mixing prior to distribution.

In some cases, downward flow of plasma or other separated fluid through axial port 64 may be restricted by surface tension. In such case, it may be desirable to provide means, such as wicking fibers 93, which can disrupt the surface tension and allow the desired flow from receptacle region 65 into the collection chamber 90. Alternatively, the surface tension can be disrupted by abruptly stopping the spinning of the rotor 10 after separation has been achieved. Such cessation of spinning will cause the fluid to wet the wall of the region 65, allowing downflow.

Referring now to FIGS. 7-11, the method of the present invention using the centrifugal rotor 10 as just described will be described in detail. Initially, reagent chamber 80 will be filled with reagent to a desired volume. As illustrated, the chamber 80 is entirely filled, but it is also possible that the chamber will be partially filled. The reagent may be loaded into rotor 10 either at a central preparation facility or immediately prior to use by the user. In the later case, the reagent may be filled using a pipette through vent port 24.

Figure 7:
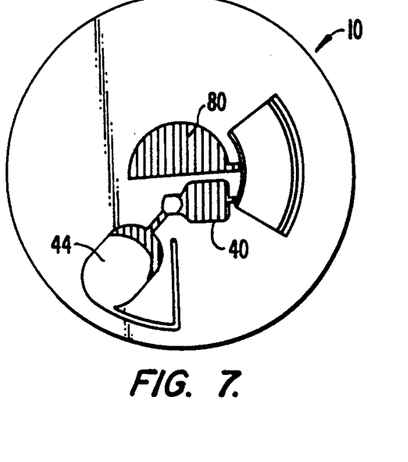
FIGS. 7-11 illustrate the method of the present invention utilizing the centrifugal rotor of FIG. 1.

Whole blood may be loaded onto the rotor 10 through application port 24 in a volume greater than that which can be accommodated by measuring chamber 40. As soon as the blood is applied through port 22, it will begin to flow laterally both into the main portion of chamber 40 and through passage 46 into overflow chamber 44 by capillary action. Since the flow area into measuring chamber 40 is substantially larger than that through passage 46, the measuring chamber will quickly fill with blood, with the overflow passing into overflow chamber 44. In this way, the blood applied through port 22 need not be carefully measured prior to application. After a time sufficient for the blood to partition between measuring chamber 40 and overflow chamber 44, the distribution of blood will be as illustrated in FIG. 7 with the capillary portion of chamber 40 being completely filled and overflow chamber 44 being partially filled.

Figure 8:
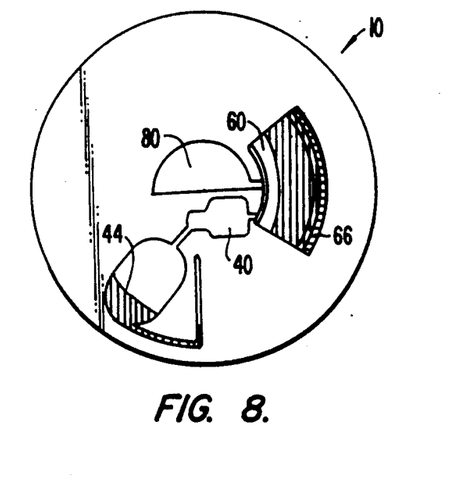

Referring now to FIG. 8, after the reagent has been added to chamber 80 and the whole blood has partitioned between chamber 40 and 44, the rotor 10 will be centrifuged or spun at a rate sufficient to cause the blood from chamber 40 and reagent from chamber 80 to flow into separation chamber 60. Additionally, the blood in overflow chamber 44 will flow radially outward, as illustrated. Conveniently, the rotor 10 will be spun at a rate in the range from about 1500 rpm to 5000 rpm, more usually from about 2500 rpm to 4000 rpm, for a time in the range from about 20 seconds to 5 minutes, more typically being about 1 minute to 3 minutes, so that the cellular components of the blood will flow into trap 66 while the plasma will remain generally in the open portion of separation chamber 60.

Figure 9:
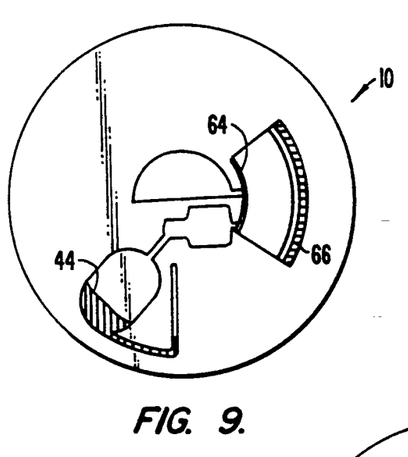
Figure 10:
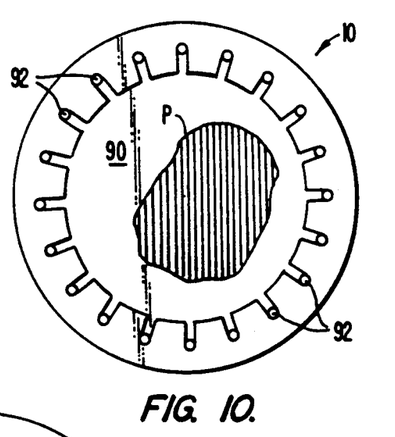
Figure 11:
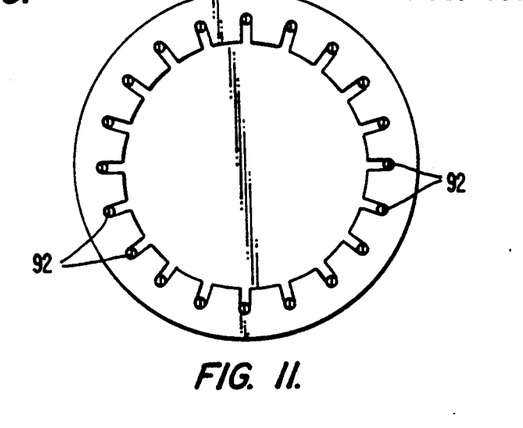

After the separation of plasmas from the cellular components of the whole blood has been completed, spinning of the rotor 10 will be stopped and the separated plasma will flow downward through axial passage 64, as illustrated in FIGS. 9 and 10. The cellular components remain in cell trap 66, and the overflow blood remains in overflow chamber 44 while the plasma has flowed downward into a pool P in collection chamber 90. The plasma may then be distributed substantially equally into the individual test wells 92 by further rotation of the rotor 10, typically at a rate in the range from about 900 rpm to 5000 rpm for a time in the range from about 10 seconds to 1 minute. After the desired distribution has been achieved, the rotor 10 may be removed from the centrifuge and the rotor transferred to an appropriate instrument, such as a spectrophotometer or fluorometer, for testing.

Figure 12:
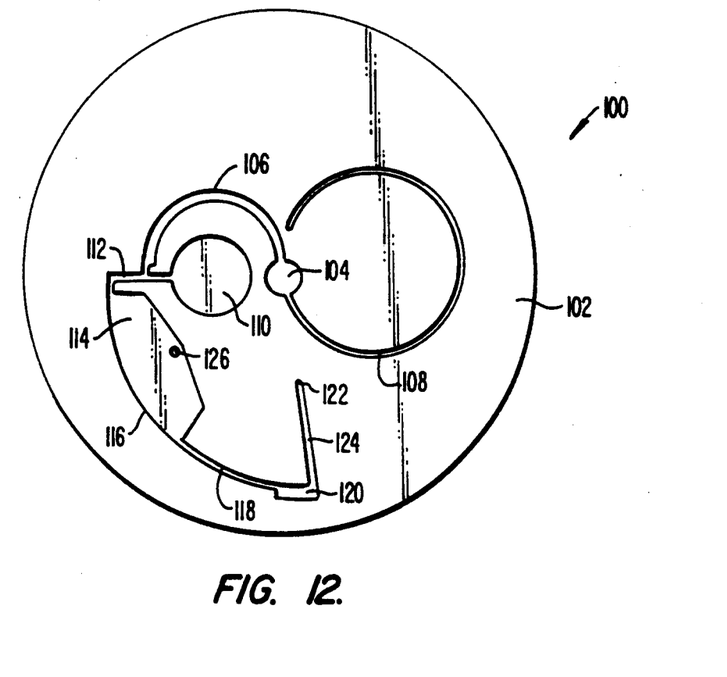
FIG. 12 illustrates an alternate embodiment of the centrifugal rotor of the present invention.

Referring now to FIG. 12, an alternate rotor construction 100 will be described. The rotor 100 will generally be a laminate structure similar to rotor 10, with only a middle layer 102 being illustrated in FIG. 12. The upper layer will include an application port (not illustrated) which is aligned with an entry chamber 104 formed in the upper surface of layer 102. The entry chamber 104 is generally aligned with the vertical (spinning) axis of the rotor 100, and a pair of passages 106 and 108 extend radially outward from said entry port. Chamber 106 serves as the measuring chamber and has a larger cross-sectional area than passage 108 so that it will fill more rapidly. Chamber 108 serves as the overflow chamber so that it can take up any excess blood which is applied through entry chamber 104. A reagent chamber 110 is located radially outward from the entry chamber 104 and connects with a non-capillary passage 112, which is connected with the distal end of chamber 106 and extends generally radially outward.

After blood is applied through entry chamber 104 so that measuring passage 106 is filled and reagent is loaded into chamber 110, the rotor 100 may be spun to cause both the blood from passage 106 and reagent from chamber 110 to flow outward through passage 112 into a separation chamber 114. Continued spinning of the rotor 100 causes the cells generally to collect along the radially-outward wall 116 of chamber 114, and further to flow down a spirally-outward path 118 to collect in cell trap 120. The separation chamber 114 and cell trap 120 are vented through the terminal end 122 of event path 124. Once the desired separation of plasma has been achieved, spinning of the rotor 100 will be stopped, and the plasma allowed to flow downward by gravity through a drainage port 126 formed at the radially-inward periphery of separation chamber 114. Usually, the bottom floor of chamber 114 will be sloped downward in the inward radial direction to promote the drainage of plasma through port 126. A collection chamber will be formed beneath the drainage port 126 in a manner similar to that illustrated in FIGS. 1-6.

Although the foregoing invention has been described in detail for purposes of clarity of understanding, it will be obvious that certain modifications may be practiced within the scope of the appended claims. In particular, it will be appreciated that two or more metering chambers, separation chambers, and collection chambers may be provided in order to run simultaneous tests and assays which require different test conditions. For example, multiple metering chambers may be provided to allow combination with different reagents or diluents in isolated separation chambers. Alternatively, a single metering chamber may be connected by separate capillary passages to control flow into separate separation chambers. In either case, assays and tests requiring different protocols can be carried out in a single rotor system.

What is claimed is:

1. A centrifugal rotor having a separation chamber and means for introducing a fluid including cellular material and a liquid phase to said chamber, wherein the separation chamber includes a receptacle region, a cell trap spaced radially outward from the receptacle region, and a capillary region between the receptacle region and the cell trap, whereby cellular material will separate from the liquid phase in the receptacle and will flow through the capillary region into the cell trap as the rotor is spun, wherein the capillarity of the capillary region is broken at the boundaries with the receptacle region and the cell trap to inhibit back flow of the cellular material into the receptacle after spinning of the rotor ceases.

2. A centrifugal rotor as in claim 1, wherein the capillary region is an annular space having inner and outer arcuate boundaries formed between opposed surfaces.

3. A centrifugal rotor as in claim 2, wherein the cell trap is an annular well contiguous with the outer arcuate boundary of the annular space of the capillary region.

4. A centrifugal rotor as in claim 2, wherein the receptacle region is a tapered compartment having a narrow aperture which is contiguous with the inner arcuate boundary of the annular space of the capillary region.

5. A blood separator comprising:
a rotor having top and bottom surfaces and a central axis;
an application well formed through the top surface of the rotor;
a metering chamber disposed within the rotor and connected to the application well;
a separation chamber disposed within the rotor and connected to the metering chamber, said separation chamber having an axial drainage port and a cell trap wherein the separation chamber is spaced radially outward from the metering chamber and the cell trap is spaced radially outward from the drainage port; and
a collection chamber disposed within the rotor below the drainage port.

6. A blood separator as in claim 5, wherein the rotor is a disk having means for mounting on a driver.

7. A blood separator as in claim 5, further comprising an overflow chamber which is connected to the application well.

8. A blood separator as in claim 7, wherein the flow rate into the overflow chamber is restricted relative to the flow rate into the metering chamber so that the metering chamber will preferentially fill with blood.

9. A blood separator as in claim 5, wherein the cell trap is divided from the remainder of the separation chamber by a capillary barrier which prevents backflow of cells from the cell trap.

10. A blood separator as in claim 5, wherein the collection chamber is a capillary volume.

11. A blood separator as in claim 5, wherein the collection chamber has dimensions larger than a capillary volume.

12. A blood separator comprising:
a rotor having top and bottom surfaces and a central axis;
an application well formed through the top surface of the rotor;
a metering chamber disposed within the rotor and connected to the application well;
a separation chamber disposed within the rotor and connected to the metering chamber, said separation chamber having an axial drainage port and a cell trap wherein the separation chamber is spaced radially outward from the metering chamber and the cell trap is spaced radially outward from the drainage port;
a collection chamber disposed within the rotor below the drainage port; and
a reagent chamber disposed within the rotor and connected to the separation chamber, wherein the reagent chamber is spaced radially inward from the separation chamber.

13. A blood separator comprising:
a rotor having top and bottom surfaces and a central axis;
an application well formed through the top surface of the rotor;
a metering chamber disposed within the rotor and connected to the application well;
a separation chamber disposed within the rotor and connected to the metering chamber, said separation chamber having an axial drainage port and a cell trap wherein the separation chamber is spaced radially outward from the metering chamber and the cell trap is spaced radially outward from the drainage port; and
a collection chamber disposed within the rotor below the drainage port wherein the collection chamber includes a plurality of examination wells about its periphery.

14. A blood separator and plasma distribution device, said device comprising:
a rotor having top and bottom surfaces and a central axis;
an application well formed through the top surface of the rotor;
means disposed at a first level within the rotor for receiving blood from the application well and separating the blood into plasma and cellular components in response to rotation of the rotor, said receiving and separating means including a drainage port opening downward through the bottom of the first level which allows only the plasma to flow downward when rotation is stopped; and a collection chamber disposed at a second level within the rotor beneath the drainage port and including a plurality of examination wells about its periphery whereby further rotation of the rotor causes plasma to flow radially outward into said wells.

15. A blood separator and plasma distribution device as in claim 14, wherein the means for separating blood comprises:
 a metering chamber disposed within the rotor;
 a separation chamber disposed within the rotor and connected to the metering chamber, said separation chamber including the axial drainage port and a cell trap wherein the separation chamber is spaced radially outward from the metering chamber and the cell trap is spaced radially outward from the drainage port.

16. A blood separator and plasma distribution device as in claim 15, wherein the rotor is a disk having means for mounting on a driver.

17. A blood separator and plasma distribution device as in claim 15, further comprising an overflow chamber and an application well formed through the top surface, wherein the application well is connected to both the metering chamber and the overflow chamber.

18. A blood separator and plasma distribution device as in claim 17, wherein the flow rate into the overflow chamber is restricted relative to the flow rate from the application well into the metering chamber so that the metering chamber will preferentially fill with blood.

19. A blood separator and plasma distribution device as in claim 15, wherein the cell trap is divided from the remainder of the separation chamber by a capillary barrier which prevents backflow of cells from the cell trap.

20. A blood separator and plasma distribution device as in claim 15, wherein the collection chamber is a capillary volume.

21. A blood separator and plasma distribution device as in claim 15, wherein the collection chamber has dimensions larger than a capillary volume.

22. A blood separator as in claim 15, further comprising a reagent chamber disposed within the rotor and connected to the separation chamber, wherein the reagent chamber is spaced radially inward from the metering chamber.

23. A blood separator as in claim 14, further comprising means disposed at a first level within the rotor for combining a reagent with the separated plasma in response to rotation of the rotor.

24. A method for separating cells from a biological fluid, said method comprising the following steps:
 (a) partitioning the biological fluid between a measuring chamber and an overflow chamber on a rotor;
 (b) rotating the rotor to cause the fluid in the measuring chamber to flow radially outward into a separation chamber where cellular components separate into a cell trap leaving separated fluid in the separation chamber; and
 (c) stopping rotation of the rotor to allow separated fluid in the separation chamber to flow :downward by gravity into a collection chamber.

25. A method as in claim 24, wherein rotation of the rotor in step (b) further causes a reagent in a reagent chamber to flow radially outward into the separation chamber, whereby the reagent combines with the separated fluid.

26. A method as in claim 24, further comprising step (d) including rotating the rotor to cause the separated fluid in the collection chamber to flow radially outward into a plurality of test wells.

27. A method as in claim 26, further comprising step (e) including examining the fluid present in the test wells.

28. A method as in claim 24, wherein step (a) takes place while the rotor is substantially stationary.

29. A method as in claim 28, wherein step (a) includes introducing the biological fluid to an open well intermediate the measuring chamber and the overflow chamber, wherein partitioning takes place by capillary action.

* * * * *